US00PP19638P2

(12) United States Plant Patent
Kordes

(10) Patent No.: US PP19,638 P2
(45) Date of Patent: Jan. 20, 2009

(54) MINIATURE ROSE PLANT NAMED 'KORPEDIA'

(50) Latin Name: *Rosa hybrida*
Varietal Denomination: KORpedia

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/787,183

(22) Filed: Apr. 13, 2007

(51) Int. Cl.
*A01H 5/00* (2006.01)

(52) U.S. Cl. ..... Plt./117
(58) Field of Classification Search ..... Plt./117
See application file for complete search history.

(56) References Cited

PUBLICATIONS

QZ (CPVO) U.S. Appl. No. 2006/0370, filed Apr. 15, 2006.

*Primary Examiner*—Annette H Para
*Assistant Examiner*—S. B. McCormick-Ewoldt

(57) ABSTRACT

A new and distinct variety of rose with long lasting, novel white flowers, and attractive foliage with excellent disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpedia'.

BACKGROUND OF THE INVENTION

The new variety of rose plant of the present invention originated from a controlled crossing in a breeding program of two distinct parents during the summer of 2002. The crossing was between 'KORamgat', a patented rose described and illustrated in U.S. Plant Pat. No. 15,612 issued on Mar. 1, 2005, and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpedia'.

SUMMARY OF THE INVENTION

The new rose plant may be distinguished from its seed parent, 'KORamgat' by the following combination of characteristics:

1. The flower color of 'KORpedia' is cream-white, while the flower color of 'KORamgat' is yellow.
2. 'KORpedia' is moderately fragrant, while 'KORamgat' exhibits little to no fragrance.

The new rose plant may be distinguished from its pollen parent, an un-named seedling by the following combination of characteristics:

1. The flower size of 'KORpedia' is large, while the flower size of the un-named seedling is medium.
2. 'KORpedia' exhibits good resistance to mildew, while the un-named seedling shows low resistance to mildew.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers.

This combination of qualities is not present in prior rose cultivars. These objectives have been substantially achieved and in that distinguish 'KORpedia' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting resulting seedlings exhibited distinctive physical and biological characteristics. The new rose plant 'KORpedia' was selected in May, 2003 from the seedling beds to be asexually propagated for further evaluation. The first asexual propagation of 'KORpedia' was done by budding to seedling understocks in July, 2003 at the inventor's nursery in Offenseth-Sparrieshoop, Germany.

This initial and other subsequent propagations conducted in controlled environments demonstrate that 'KORpedia' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds and flowers of 'KORpedia'. Specifically illustrated is: a flower bud, partially opened bloom, open bloom, floral parts, and flower sepals.

DETAILED BOTANICAL DESCRIPTION

The following is a description of 'KORpedia', as observed growing in July, 2007 in a greenhouse in Hamberg, Germany on plants of four months of age. Color references are made using The Royal Horticultural Society (London, England) Colour Chart, 2001 except where common terms of color are used.

For a comparison, several physical characteristics of the rose variety 'KORkleiva', a rose variety from the same inventor described and illustrated in U.S. Plant Pat. No. 11,232 and issued on Mar. 23, 1998 are compared to 'KORpedia' in Chart 1.

CHART 1

| Characteristic | 'KORpedia' | 'KORkleiva' |
|---|---|---|
| Diameter, open flower bloom | 60 mm | 40-45 mm |
| Length of flower bud, upon opening | 30 mm | 19 mm |
| Bud color, as sepals first unfold | White Group 155B | Orange-White Group 159C |

Parents:

*Seed parent.*—'KORamgat'.

*Pollen parent.*—An un-named seedling.

Classification:

*Botanical classification.*—*Rosa hybrida,* 'KORpedia'.

*Commercial classification.*—Miniature rose.

FLOWER AND FLOWER BUD

*Blooming habit.*—Continuous.

*Flower bud.*—Size: Upon opening, 30 mm in length from base of receptacle to end of bud and 20 mm diameter at its widest point. Bud form: Long and high-centered. Bud color: As sepals first unfold, bud color is White Group 155B. When ¼ open, the upper surface of petals is Yellow Group Group 8D, and the lower surface is White Group 157D. Guard petals with intonations of Green Group 146D.

*Sepals.*—Size: Average 30 mm long×7 mm wide. Shape: Sepals generally subulate. Sepal apex generally comes to a long narrow point. Strong foliaceous appendages on three of the five sepals. Base is flat at union with receptacle. Quantity: Five. Margins: Limited to no stipitate glands on margins. Surface texture: Inner side: Rough and grooved. With fine white hairs. Outer side: Smooth. Color: Upper surface: Green Group 146A. Lower surface: Green Group 146C.

*Receptacle.*—Surface: Smooth. Color: Yellow-Green Group 144B. Shape: Urn shaped. Size: 7 mm (h)×8 mm (w).

*Peduncle.*—Surface: Smooth. Length: 20–35 mm average length. Diameter: 4–6 mm average diameter. Color: Yellow-Green Group 146C. Strength: Strong. Borne: Singly.

Flower bloom:

*Fragrance.*—Moderate fruity fragrance.

*Duration.*—On the plant 20–22 days. Long lasting. Senesced petals drop away cleanly.

*Size.*—Medium flowered pot rose. When open, the average flower diameter is 60 mm and the average flower height is 35 mm.

*Form.*—Shape of flower when viewed from the side: Upon opening, upper part: Flattened convex. Upon opening, lower part: Flattened convex. Open flower, upper part: Flat. Open flower, lower part: Flattened convex.

Color:

*Upon opening, petals.*—Outermost petals: Outer Side: Green-White Group 157B with upper edges of margins Yellow-Green 144D. Inner Side: Green-White Group 157B with upper edges of margins Yellow-Green 144D. Innermost petals: Outer Side: Yellow Group 4D. Inner Side: Yellow Group 2D.

*Upon opening, basal petal spots.*—Basal petal spot, outermost petals: Outer Side: No distinctive coloration observed. Inner Side: Yellow Group 2C. Basal petal spot, innermost petals: Outer Side: No distinctive coloration observed. Inner Side: Yellow Group 4B.

*After opening, petals.*—Outermost petals: Outer Side: Yellow Group 4D. Inner Side: Yellow Group 2D. Innermost petals: Outer Side: Yellow Group 4D. Inner Side: Yellow Group 2D. After opening, no distinctive coloration at petal base observed. Variegations: Intonations on the guard petals of Green Group 143C.

General tonality: On open flower Yellow Group 2D. No change in the general tonality at the end of the 6th day. Afterwards, general tonality is Yellow-White Group 158B.

Petals:

*Petal count.*—Approximately 30–35 petals under normal conditions.

*Petal reflex.*—Petals reflex slightly.

*Petal edge.*—Ruffled.

*Petal shape.*—Round. Apex shape is pointed. Shape of base is rounded.

*Petal size.*—30–35 mm long; 25–35 mm wide.

*Thickness.*—Thick.

*Petal arrangement.*—Generally in a regular pattern with overlapping edges.

Petaloids: Present.

*Petaloid count.*—Average of 6–8 per flower.

*Petaloid edge.*—Smooth.

*Petaloid texture.*—Wrinkled.

*Petaloid shape.*—Obovate. Base: Comes to a point. Acute. Apex: Rounded. Entire.

*Petal size.*—Petaloids are 10–15 mm long and 6–8 mm wide.

*Petaloid color.*—Color of inner side is Yellow Group 4D. Color of outer side is Yellow Group 4D.

Reproductive organs:

*Pistils.*—Approximately 90 present. Stigmas: Location: At same position as anthers. Color: Green-Yellow Group 1D. Styles: Length: 5 mm long. Color: Green-Yellow 1D.

*Stamens.*—Approximately 110–120 on average and regularly arranged. Anthers: Size: 2.5–3.0 mm long. Color: Yellow-Orange Group 20A. Pollen: Absent. Filaments: Color: Yellow Group 12B. Length: 5 mm.

THE PLANT

*Plant growth.*—Moderately vigorous. Upright to bushy. When grown as a 15 cm container plant, the average height of the plant itself is 22 cm and the average width is 18–20 cm. When grown from rooted cuttings, the instant plant roots readily in less than 14 days.

*Stems.*—Stem color: Young wood: Green Group 138A. Older wood: Green Group 138A. Stem surface: Young wood: Smooth. Older wood: Smooth.

*Prickles.*—Present. Incidence: Few. 3–4 per 10 cm of stem. Size: Average length: 4 mm. Color: Immature prickles: Greyed-Yellow Group 162D. Mature prickles: Greyed-Purple Group 185D. Senescing to Greyed-Orange Group 177A. Shape: Linear. Anthocyanin: Limited on immature prickles. Color: Greyed-Purple Group 185C.

*Leaves and leaflets.*—Normally 5 leaflets on normal leaves in middle of the stem. Leaf size: 80 mm (1)× 65 mm (w). Quantity: Abundant. Texture: Upper side of leaflet: Matte and smooth. Under side of leaflet: Matte and smooth. Color, mature foliage: Upper Leaf Surface: Green Group 147A. Lower Leaf Surface: Green Group 147B. Color, juvenile foliage: Upper Leaf Surface: Green Group 147A. Lower Leaf Surface: Green Group 147B. Anthocyanin intonation: Very limited. Location: Intonations present on juvenile leaf margins, petiole, rachis, and sepals. Color: Greyed-Purple Group 185B.

*Stipules.*—Size: 14 mm long. 6 mm between the tips of the stipule. Main body of stipule 6 mm in width. Shape: Apex: Longitudinally flanged or winged. Base: Inverted semi-circle. Stipule color: Margins: Green Group 138A. Center: Yellow-Green Group 145B. Anthocyanin intonations of Greyed-Purple Group 184B. Presence of stipitate glands: Limited amount present on margins. Margins: Serrated. With limited stipitate glands.

*Petiole.*—Length: 8–10 mm. Diameter: 1.5 mm. Petiole color: Green Group 144A. Faint anthocyanin intonations present on juvenile tissue. Color: Greyed-Purple Group 184B. Underneath: Smooth, with a few stipitate glands underneath and an occasional prickle. Stipitate glands: Limited numbers of stipitate glands on margins.

*Petiole rachis.*—Length: 12 mm. Diameter: 1.5 mm. Color: Green Group 147A. Faint anthocyanin intonations present on juvenile tissue. Color: Greyed-Purple Group 184B. Margins: Smooth, with a few stipitate glands underneath. Prickles: A few small prickles underneath. Stipitate glands: Limited numbers of stipitate glands on margins.

*Leaflets.*—Size: Average size of the terminal leaflet is 45 mm (l)×25 mm (w). Shape: Ovate. Base: Ovate. Apex: Acute. Margins: Serrated. Texture: Thick.

Hips/seed formation: None observed. Winter hardiness: To date, the variety has been grown successfully in Zone 7.

Disease resistance: Excellent resistance to powdery mildew and Botrytis under normal greenhouse growing conditions.

I claim:

1. A new and distinct variety of rose plant characterized by the following combination of characteristics:

(a) Forms attractive, long lasting white flowers;

(b) Exhibits upright growth habit;

(c) Propagates well using traditional methods, and;

(d) Exhibits excellent resistance to disease under normal growing conditions, substantially as herein illustrated and described.

* * * * *

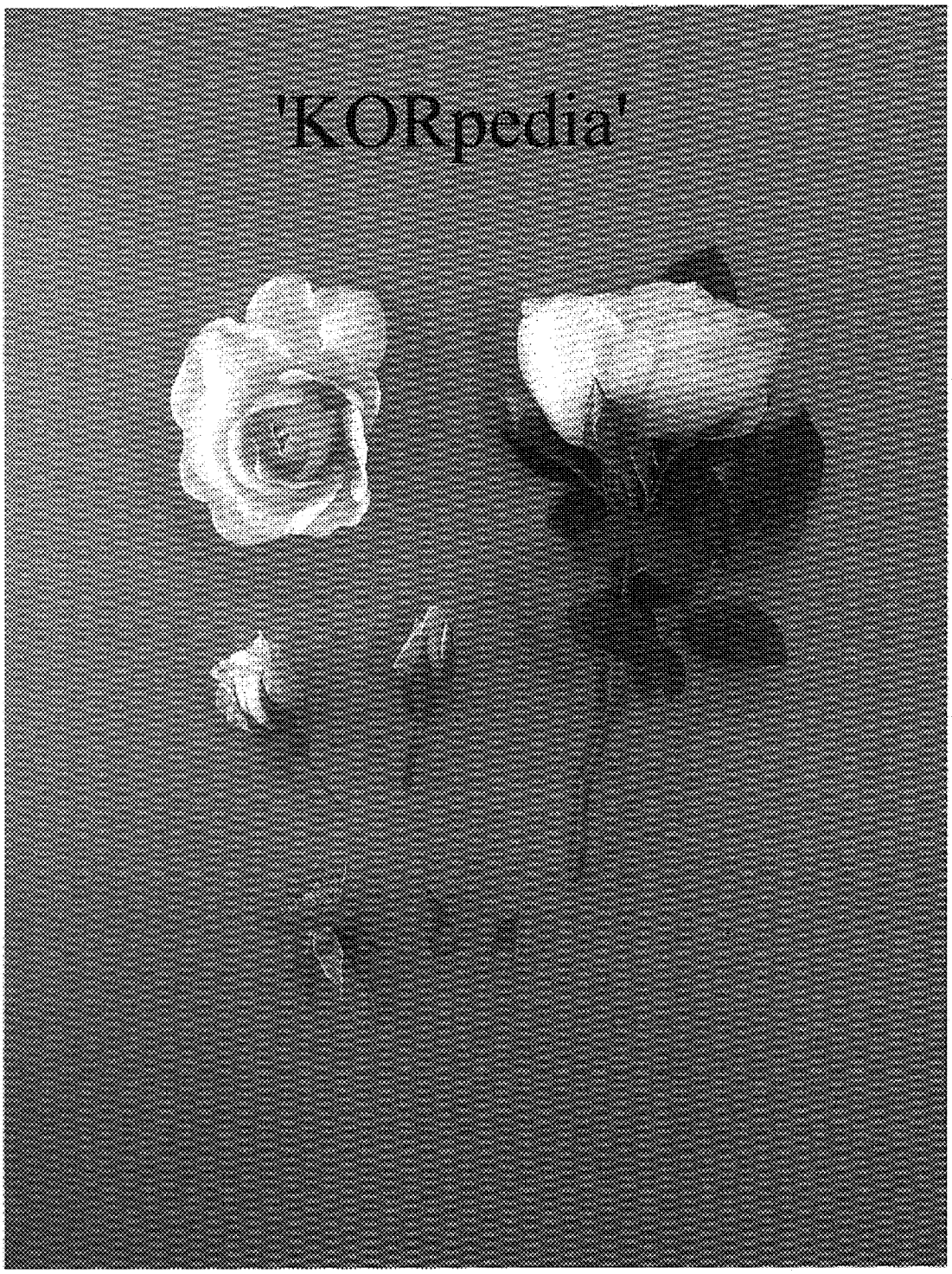
'KORpedia'